US007632817B2

(12) United States Patent (10) Patent No.: US 7,632,817 B2
Granier et al. (45) Date of Patent: Dec. 15, 2009

(54) PEPTIDE DECOYS FOR THE PREPARATION OF MEDICAMENTS INTENDED FOR THE PREVENTION OR TREATMENT OF AUTOIMMUNE PATHOLOGIES OR DISORDERS LINKED TO THE APPEARANCE OF ANTIBODIES DIRECTED AGAINST EXOGENOUS PROTEINS

(75) Inventors: Claude Granier, Clapiers (FR); Sylvie Villard, Montpellier (FR)

(73) Assignee: Centre National de la Recherche Scientifique, Paris (FR)

( * ) Notice: Subject to any disclaimer, the term of this patent is extended or adjusted under 35 U.S.C. 154(b) by 705 days.

(21) Appl. No.: 10/492,929

(22) PCT Filed: Oct. 17, 2002

(86) PCT No.: PCT/FR02/03557

§ 371 (c)(1),
(2), (4) Date: Dec. 14, 2004

(87) PCT Pub. No.: WO03/040176

PCT Pub. Date: May 15, 2003

(65) Prior Publication Data

US 2005/0124544 A1 Jun. 9, 2005

(30) Foreign Application Priority Data

Oct. 17, 2001 (FR) .................................. 01 13360

(51) Int. Cl.
*A61K 38/08* (2006.01)
*A61K 38/10* (2006.01)
(52) U.S. Cl. ........................... 514/14; 514/15; 530/327; 530/328
(58) Field of Classification Search ........................ None
See application file for complete search history.

(56) References Cited

U.S. PATENT DOCUMENTS 5,187,155 A      2/1993   Fair
5,846,933 A  *  12/1998   Korngold et al. ............... 514/11
6,043,220 A  *   3/2000   Chang et al. .................... 514/12

FOREIGN PATENT DOCUMENTS

| WO | 96/02572 | 2/1996 |
| WO | 98/33920 | 8/1998 |
| WO | 99/30736 | 6/1999 |
| WO | 99/46274 | 9/1999 |
| WO | 99/47932 | 9/1999 |
| WO | 00/40602 | 7/2000 |

OTHER PUBLICATIONS

U.S. Departmetn of Health and Human Services, Office of Women's Health. Autoimmune Diseases: Overview. pp. 1-6. Jan. 2005.*
Rudinger, J (1976). Peptide Hormones (Ed. J.A. Parson). University Park Press. baltomre pp. 1-7.*
Bellone et al. 'Cancer Immunotherapy: Synthetic and Natural Peptides in the Balance' Immunol Today. Oct. 1999;20(10):457-62.*
Bradley et al. 'Limits of Cooperativeity in a Structurally Modula Protein: Response of the Notch Ankyrin Domain to Analogous Alanine Substitution in Each Repeat.' J. Mol. Biol. vol. 324, pp. 373-386 2002.*
Vandenbark et al. 'TCR Peptide Therapy in Human Autoimmune Diseases' Neurochemcial Research, vol. 26, No. 6, pp. 713-730. 2001.*
Lim et al. 'Allelic Avation of MHC Structure Allters Peptide Ligands to Induce Atypical Partial Agonistic CD8+ T Cell Function.' J. of Exper. Med. vol. 198, No. 1, pp. 99-109. Jul. 2003.*
Steinman et al. 'How to Successfully Apply Animal Studies in Experimental Allergic Encephalomyelitis to Research on Multple Sclerosis' Ann Neurol. vol. 60, pp. 12-21. 2006.*
Ngo et al. "Computational Complexity, Protein Structure Prediction, and the Levinthal Paradox." TheProtein Folding Problem and Tertiary structure Prediction. Ed. K. Merz and L. Le Grand. Birkhauser, Boston, Ma. 491-495.*
Berendsen, Herman. "A Glimpse of the Holy Grail?" Science, vol. 282, pp. 642-643. Oct. 23, 1998.*
McConnell, S J et al., "Constrained peptide libraries as a tool for finding mimotopes" Gene, vol. 151, Dec. 30, 1994, pp. 115-118.
Sem, D S et al., "Structural characterization and optimization of antibody-selected phage library mimotopes of an antigen associated with autoimmune recurrent thrombosis" Biochemistry, vol. 37, No. 46, Nov. 17, 1998, pp. 16069-16081.
Nogami et al., "Identification of a factor VIII peptide, residues 2315-2330, which neutralizes human factor VIII C2 inhibitor alloantibodies: Requirement of Cys2326 and Glu2327 for maximum effect." British Journal of Haematology, vol. 107, No. 1, Oct. 1999 , pp. 196-203, XP009008081 ISSN: 0007-1048.
Kuwabara et al., "Mapping of the minimal domain encoding a conformational epitope by lambda phage surface display: factor VIII inhibitor antibodies from haemophilia A patients," Journal of Immunological Methods, Elsevier Science Publishers B.V., Amsterdam, NL, vol. 224, No. 1-2, Apr. 22, 1999 , pp. 89-99, XP004165513 ISSN: 0022-1759.
Voorberg et al., "Phage display technology: A tool to explore the diversity of inhibitors to blood coagulation factor VIII." Seminars in Thrombosis and Hemostasis, vol. 26, No. 2, pp. 143-150, XP008005330 ISSN: 0094-6176.

(Continued)

*Primary Examiner*—Anish Gupta
(74) *Attorney, Agent, or Firm*—Young & Thompson

(57) ABSTRACT

Peptide or pseudopeptide decoys binding to antibodies capable of being developed against endogenous proteins within the framework of autoimmune pathologies or against exogenous proteins administered to patients, in particular within the framework of pathologies due to a deficiency in these proteins, the amino acid sequence of the peptide or pseudopeptide decoys differing from that of the epitopes recognized by the antibodies, for the preparation of medicaments intended for the prevention or treatment of the autoimmune pathologies, or for the prevention or treatment of the disorders linked to the appearance of antibodies directed against the exogenous proteins.

3 Claims, 3 Drawing Sheets

OTHER PUBLICATIONS

Figure 1:
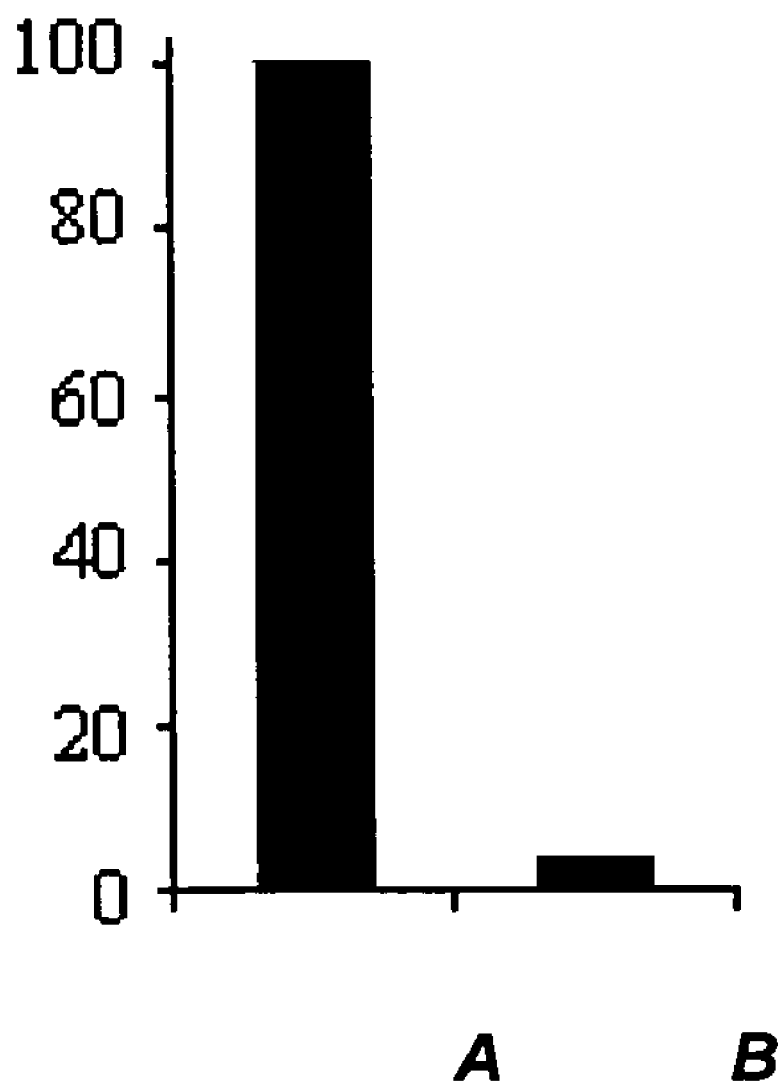

Ferrieres et al. "Affinity for the cognate monoclonal antibody of synthetic peptides derived from selection by phage display: Role of sequences flanking the binding motif." European Journal of Biochemistry, vol. 267, No. 6, Mar. 2000, pp. 1819-1829, XP001093880 ISSN: 0014-2956.

Takahaashi et al. "Change of Antigenic and Neutralizing specificity in Substitutional epitope peptides of hemophilia B inhibitor" Peptides, Elmsford, US, vol. 19, No. 7, 1998, pp. 1129-1136, XP001037525 ISSN: 0196-9781.

McConnell et al. "Constrained peptide libraries as a tool for finding mimotopes" Gene, Elsevier Biomedical Press. Amsterdam, NL, vol. 151, No. 1, Dec. 30, 1994, pp. 115-118, XP004042621 ISSN: 0378-1119.

Sibille et al. "Mimotopes of Po;yreactive Anti-DNA Antibodies identified Using Phage-Display Peptide Libraries", European Journal of Immunology, Weinheim, DE, vol. 27, May 1997, pp. 1221-1228, XP000973084 ISSN: 0014-2980.

Doudna et al. "Selection of an RNA molecule that mimics a major autoantigenic epitope of human insulin receptor" Proceedings of the National Academy of Sciences of USA, National Academy of Science, Washington, US, vol. 92, No. 6, Mar. 14 (1995), pp. 2355-2359, XP000919062 ISSN: 0027-8424.

Vanhoorelbeke et al. "Sequence alignment between VWF and peptide inhibiting the VWF-collagen interaction does not result in the identification of a collagen-binding site in VWF" Thrombosis and Haemostasis, Stuttgart, DE, vol. 84, No. 4, Oct. 2000, pp. 621-625, XP008006899 ISSN: 0340-6245.

Suphioglu et al. "A novel grass pollen allergen mimotope identified by phage display peptide library inhibits allergen-human IgE antibody interaction" FEBS Letters, Elsevier Science Publishers, Amsterdam, NL, vol. 502, No. 1-2, July 27, 2001, pp. 46-52, XP004296817 ISSN: 0014-5793.

Sem et al. "Structural characterization and optimization of antibody-selected phage library mimotopes of an antigen associated with autoimmune recurrent thrombosis." Biochemistry. United States Nov. 17, 1998, vol. 37, No. 46, Nov. 17, 1998, pp. 16069-16081, XP002245692 ISSN: 0006-2960.

* cited by examiner

PEPTIDE DECOYS FOR THE PREPARATION OF MEDICAMENTS INTENDED FOR THE PREVENTION OR TREATMENT OF AUTOIMMUNE PATHOLOGIES OR DISORDERS LINKED TO THE APPEARANCE OF ANTIBODIES DIRECTED AGAINST EXOGENOUS PROTEINS

A subject of the invention is peptide decoys of pathogenic antibodies for the preparation of medicaments intended for the prevention or treatment of autoimmune pathologies, or disorders linked to the appearance of antibodies directed against exogenous proteins which are recombinant or non-recombinant used within the framework of the treatment of these autoimmune pathologies or pathologies requiring the administration of said exogenous proteins to patients.

Hemophilia A is a (severe) pathology due to the absence or insufficiency of functional factor VIII (FVIII). The coagulation capacity is restored in patients by the administration of concentrates of factor VIII which is recombinant or originates from plasmas.

It is known that in a considerable percentage (approximately 15-25%) of hemophilia A patients treated with factor VIII, an auto-immunization process leads to the appearance of anti-FVIII antibodies inhibiting the procoagulant function of the factor VIII administered, making the treatment of the patients still more complex. These antibodies bind to several regions (or structural domains) of the FVIII protein, in particular the C2, A2 and a3-A3-C1 domains.

The antibody response has the effect of inhibiting the procoagulant activity of the FVIII administered and thus seriously complicating the treatment of these hemophiliacs.

No current therapy completely resolves this problem; "immunological tolerization" by administration of massive doses of factor VIII has a considerable economic cost to the health system, which makes research necessary in order to develop more cost-effective processes.

It is known that antibodies have a specialized molecular structure, called a paratope, which allows them to perform an important biological finction: the recognition of the antigen.

The paratope of the antibody is capable of recognizing not only a limited part (called the "epitope") of the antigen which was at the origin of its selection, but also smaller fragments of this antigen, in particular peptides corresponding to the epitope (called "epitopic peptides"), peptides possessing modifications of sequence or chemical structure relative to the epitope (called "epitope variants") or also molecules not having sequence homology with the antigen (called "mimotopes").

The antibody response against FVIII is polyclonal and heterogeneous in its specificity [Gilles et al., 1993, Blood, 2452-61] but it has been observed that the regions recognized by the inhibitor antibodies (epitopes) are restricted to a few principal zones of the factor VIII molecule. The A2 domain and the C2 domain were initially identified by immnunodot methods using proteolytic fragments of FVIII [Fulcher et al., 1985, PNAS USA 82, 7728-32] and subsequently confirmed when the nucleotide sequence of FVIII was determined (Vehar et al., 1984, Nature 312, 337-342; Gitschier et al., 1984, Nature 312, 326-336) and recombinant fragments prepared [Scandella et al., 1988, PNAS 86(4), 1387; Scandella et al., 1989, Blood 74, 1618-26]. In one particular case, the epitope of a murine monoclonal inhibitor antibody could be restricted to a sequence of 25 amino acids of the A2 region (residues 484-508) thanks to the judicious use of hybrids between the sequences of human and porcine factor VIII [Healey et al., 1995, J. Biol. Chem. 270, 14505-9]. The cloning of a human antibody from B lymphocytes from a hemophilia patient made it possible to show that this antibody recognized the C2 domain and inhibited the FVIII function probably by binding with a strong affinity to the binding site of the von Willebrandt factor [Jacquemin et al., 1998, Blood 92, 496-506]. Finally, the a3-A3-C1 region also seems to be recognized by inhibitor antibodies.

The therapeutic approaches currently existing within the framework of combating the effects of these antibodies, are mainly the following:

- stimulation by desmopressin of the production of FVIII in moderate hemophiliacs [Kesteven et al., 1984, Thromb. Haemost. 52, 50-2];
- activation of the coagulation cascade by prothrombin complex concentrates [Lusher et al., 1983,Blood62, 1135-8];
- administration of activated human recombinant FVII [Hedner et al., 1993, Transfus. Med Rev. 7, 78-83];
- use of porcine FVIII [Hay et al., 1996, Vox Sang 70, 68-9],
- use of activated prothrombin concentrates (U.S. Pat. No. 4,160,02 (1979): Method for producing a blood-coagulation-promoting preparation for human blood plasma; U.S. Pat. No. 4,357,321 (1982): Method and composition for treating clotting factor inhibitors; U.S. Pat. No. 4,663,164 (1987): Aqueous compositions for treating blood clotting inhibitors),
- use of factor VIII fragments (U.S. Pat. No. 4,649,132 (1987): Treatment of factor VIII inhibitors; U.S. Pat. No. 4,769,336 (1987): Treatment of factor VIII inhibitors; U.S. Pat. No. 5,149,637 (1992): Recombinant factor VIII fragments),
- use of immunocomplexes (U.S. Pat. No. 5,543,145 (1996): Pharmaceutical composition and method for the suppression of factor VIII inhibitor production),
- use of hybrid human/porcine factor VIII molecules (U.S. Pat. 5,888,974: Hybrid human/animal factor VIII).

A conceptual approach of molecular decoys, not based on peptides or peptide derivatives, has recently been described in two different models of human pathologies with humoral mediation: diabetes and myasthenia gravis. In the two approaches, short sequences of RNA were selected (from a large library of RNA of random sequence) for their ability to bind specifically to a monoclonal antibody representative of the human autoantibodies [Lee et al., 1997, Nat. Biotechnol. 15, 41-5; Lee et al., 1996, J. Exp. Med. 184, 315-24; Hay et al., 1996, mentioned above]. In both cases, the authors succeed in demonstrating that the decoys selected inhibit the binding of a few serums from patients to their target (insulin receptor and acetylcholin receptor, respectively). However, these observations have not been validated in an animal model of these pathologies. One of the weaknesses of this approach is the metabolic instability of the RNAs; although modified RNAs, more resistant to the nucleases, have been used in certain of these studies, it may be thought that the plasma half-life of such molecules is sufficiently weak to remove any chance for the decoy to act.

The present invention results from the demonstration by the Inventors, that peptides or pseudopeptides corresponding to epitope variants or to mimotopes, are capable of binding in the site of anti-FVIII antibodies, by preventing their binding to factor VIII, and thus reducing the anticoagulant activity of this antibody.

The present invention aims to provide new means for combating the antibodies present in the organism within the framework of autoimmune pathologies, or pathologies requiring the administration of proteins to the patients, making it possible to considerably limit the cost of the current therapies in this field, with an effectiveness comparable to or even greater than current treatment methods.

A subject of the present invention is the use of peptide or pseudopeptide decoys binding to antibodies capable of being developed against endogenous proteins within the framework of autoimmune pathologies or against exogenous proteins administered to patients, in particular within the framework of pathologies due to a deficiency in these proteins, the amino acid sequence of said peptide or pseudopeptide decoys differing from that of the epitopes recognized by said antibodies, for the preparation of medicaments intended for the prevention or treatment of said autoimmune pathologies, or for the prevention or treatment of disorders linked to the appearance of antibodies directed against said exogenous proteins.

A subject of the invention is more. particularly the abovementioned use of peptide or pseudopeptide decoys defined above, comprising between approximately 6 and approximately 20 natural or non-natural amino acids (and preferably between approximately 8 and approximately 16 of these amino acids), said decoys being selected for their ability to:
  inhibit in vitro and in vivo the binding of antibodies to proteins specifically recognized by the latter within the framework of autoimmune pathologies, or pathologies requiring the administration of said proteins to patients,
  restore in vitro and in vivo the activity of said proteins in the presence of said antibodies.

Advantageously, the antibodies preferentially recognize the peptide or pseudopeptide decoys rather than the abovementioned endogenous or exogenous proteins.

The invention also relates to the abovementioned use of decoys as defined above, for the preparation of medicaments intended for the prevention or treatment:
  of autoimmune pathologies such as:
    myasthenia gravis,
    the appearance of autoantibodies directed against insulin,
    the appearance of autoantibodies directed against factor VIII or IX within the framework of autoimmune variants of hemophilia A or B respectively, in particular in pregnant women in the case of hemophilia A,
    the appearance of anti-sperm autoantibodies responsible for certain cases of infertility,
  or disorders linked to the appearance of antibodies directed against exogenous proteins, or against the recombinant endogenous proteins synthesized with a view to a gene therapy, said proteins being administered within the framework of the treatment of pathologies due to a deficiency in these proteins, such as hemophilia A or B.

A subject of the invention is more particularly the use of decoys as defined above, for the preparation of medicaments intended for the prevention or treatment of disorders linked to the appearance of antibodies against endogenous factor VIII, or against exogenous factor VIII or derivatives, recombinant or non-recombinant, administered within the framework of hemophilia A.

The invention also relates to the abovementioned use of peptide decoys defined above, as obtained from vectors expressing peptide libraries.

Therefore, a subject of the invention is more particularly the abovementioned use of decoys having no homology, or even a weak homology comprised between approximately 10% and approximately 30%, with the epitopes of said proteins recognized by said antibodies, said decoys also being designated mimotope decoys.

The invention relates more particularly to the abovementioned use of mimotope decoys of factor VIII.

A subject of the invention is more particularly the abovementioned use of mimotope decoys of factor VIII of following formula (I):

$$(X_1)_{n1}\text{-}C\text{-}Xa\text{-}C\text{-}(X_2)_{n2} \tag{I}$$

in which:
n1 and n2 independently of one another represent 0 or 1
$X_1$ and $X_2$ independently of one another represent a natural or non-natural amino acid,
$X_a$ represents a chain of 8 to 10 natural or non-natural amino acids.

The invention relates more particularly to the abovementioned use of mimotope decoys defined above of formula (1) in which:
$X_1$ is chosen from Y, E, Q, S, R, A, K, N, or T,
$X_2$ is chosen from R, T, H, G, S, L, V, P, F, D, K, A, Q or I.

A subject of the invention is more particularly the abovementioned use of mimotope decoys defined above of formula (I) in which $X_a$ represents the following sequence:

```
NPSIGDKN        SEQ ID NO: 1
```

Therefore, a subject of the invention is also more particularly the abovementioned use of the mimotope decoy of the following formula:

```
YCNPSIGDKNCR    SEQ ID NO: 2
```

The invention also relates to the abovementioned use of mimotope decoys of formula (I) in which Xa represents the sequence of the following formula:

$$(X_3)_{n3}\text{-}X_4\text{-}X_5\text{-}G\text{-}K\text{-}T\text{-}X_6\text{-}L \quad (\text{SEQ ID NO: 48})$$

in which:
$n_3$ represents 0 or 1,
$X_3$ represents any amino acid,
$X_4$ represents a hydrophobic amino acid,
$X_5$ represents an aromatic amino acid,
$X_6$ represents a hydrophobic amino acid.

A subject of the invention is more particularly the abovementioned use of mimotope decoys defined above of formula (I), characterized in that:
$X_3$ is chosen from I, Q, R, T, or K,
$X_4$ is chosen from V, T, L, I, M, F, W, or Y,
$X_5$ is chosen from F, or Y,
$X_6$ is chosen from A, M, Y, P, T; or V, Therefore, the invention relates more particularly to the abovementioned use of mimotope decoys defined above of the following formulae:

```
ECIVYGKTALCT    SEQ ID NO: 3
QCPTFGKTMLCT    SEQ ID NO: 4
SCRLFGKTYLCH    SEQ ID NO: 5
SCTVYGKTPLCG    SEQ ID NO: 6
RCKTFGKTTLCS    SEQ ID NO: 7
RCTVYGKTVLCL    SEQ ID NO: 8
```

A subject of the invention is also the abovementioned use of mimotope decoys of formula (I) in which $X_a$ represents the sequence of the following formula:

$$X_7\text{-}X_8\text{-}W\text{-}X_9\text{-}N\text{-}R\text{-}X_{10}\text{-}X_{11}\text{-}(X_{12})_{n12}\text{-}(X_{13})_{n13}$$

in which:

n12 and n13 independently of one another represent 0 or 1, $X_7$ to $X_{13}$ represent any amino acid, if appropriate W is replaced by F.

A subject of the invention is more particularly the abovementioned use of mimotope decoys defined above of formula (I), characterized in that:

$X_7$ is chosen from H, S, T, M, Q, or G, $X_8$ is chosen from T, A, K, R, Q, or E, $X_9$ is chosen from S, A, H, F, V, G, or T, $X_{10}$ is chosen from R, K, L, S, H, T, I, or A, $X_{11}$ is chosen from S, T, V, K, R, Y, M, or D, $X_{12}$ is chosen from S, R, or L, $X_{13}$ is chosen from I, H, or W.

Therefore, a subject of the invention is more particularly the abovementioned use of mimotope decoys defined above of formula (I) chosen from those of the following formulae:

| | |
|---|---|
| QCHTWSNRRSCL | SEQ ID NO: 9 |
| SCHAWSNRRTCR | SEQ ID NO: 10 |
| RCHAWSNRKSCV | SEQ ID NO: 11 |
| CSKWANRLVSIC | SEQ ID NO: 12 |
| CSKWHNRSKRHC | SEQ ID NO: 13 |
| ACTTWSNRSKCP | SEQ ID NO: 14 |
| ECTRWSNRSRCF | SEQ ID NO: 15 |
| CMKWSNRSSRWC | SEQ ID NO: 16 |
| KCGRWSNRSSCT | SEQ ID NO: 17 |
| CGRWFNRSDLHC | SEQ ID NO: 18 |
| ACHEWSNRSTCT | SEQ ID NO: 19 |
| KCSRWTNRHLCD | SEQ ID NO: 20 |
| KCTRWTNRHLCS | SEQ ID NO: 21 |
| KCTRWTNRAHCP | SEQ ID NO: 22 |
| QCSKWVNRSRCA | SEQ ID NO: 23 |
| NCQKWTNRRTCL | SEQ ID NO: 24 |
| QCGRWSNRSYCS | SEQ ID NO: 25 |
| TCHRWGNRTSCQ | SEQ ID NO: 26 |
| QCHRWANRISCS | SEQ ID NO: 27 |
| RCTQWTNRAYCP | SEQ ID NO: 28 |
| ACTQWSNRHMCG | SEQ ID NO: 29 |
| TCHPFSNRSTCT | SEQ ID NO: 30 |

A subject of the invention is also more particularly the abovementioned use of the mimotope decoy of the following formula:

| | |
|---|---|
| SCHAWSNRRTCR | SEQ ID NO: 10 |

A subject of the invention is also the abovementioned use of the mimotope decoys of the following formula:

| | |
|---|---|
| KCEPDDPWPQCI | SEQ ID NO: 31 |
| ACKRNHRWGACV | SEQ ID NO: 32 |
| ECGSHAWGRRCK | SEQ ID NO: 33 |

The invention also relates to the abovementioned use of mimotope decoys defined above of formula (I) in which $X_a$ represents the sequence of the following formula:

$$(X_{14})_{n14}\text{-}X_{15}\text{-}X_{16}\text{-}H\text{-}X_{17}\text{-}W\text{-}G\text{-}X_{18}\text{-}(X_{19})_{n19}$$

in which:

n14 and n19 independently of one another represent 0 or 1, $X_{14}$ to $X_{15}$ represent any amino acid.

The invention relates more particularly to the abovementioned use of mimotope decoys defined above of formula (1), characterized in that:

$X_{14}$ represents K, $X_{15}$ represents R, or G, $X_{16}$ represents N, or S, $X_{17}$ represents R, or A, $X_{18}$ represents A, or R, $X_{19}$ represents R.

Therefore, a subject of the invention is more particularly the abovementioned use of mimotope decoys defined above of formula (I) chosen from those of the following formulae:

| | |
|---|---|
| ACKRNHRWGACV | SEQ ID NO: 34 |
| ECGSHAWGRRCK | SEQ ID NO: 35 |

The invention also relates to the abovementioned use of peptide decoys corresponding to epitopes recognized by the antibodies present in said proteins, the peptide sequence of which is modified by suppression, substitution, or addition of at least one amino acid, said decoys being designated epitope variants.

A subject of the invention is more particularly the abovementioned use of epitope variants of factor VIII.

A subject of the invention is still more particularly the abovementioned use of epitope variants of factor VIII of the following formula (II)

(II):

(SEQ ID NO: 49)

$$(C)_{n1}\text{-}X_1\text{-}X_2\text{-}X_3\text{-}L\text{-}T\text{-}D\text{-}S\text{-}E\text{-}M\text{-}D\text{-}V\text{-}V\text{-}R\text{-}X_4\text{-}X_5\text{-}(C)_{n2}$$

in which:

n1 and n2 independently of one another represent 0 or 1, $X_1$ to $X_5$ represent any amino acid.

with the exception of the peptide of formula DDDLTDSEMDVVRFD (SEQ ID NO: 36).

The invention relates more particularly to the abovementioned use of epitope variants defined above of formula (II), characterized in that:

$X_1$ represents D or A, $X_2$ represents D or A, $X_3$ represents D or A, $X_4$ represents F, Y, or W, $X_5$ represents D or A.

Therefore, a subject of the invention is more particularly the abovementioned use of epitope variants defined above of the following formulae:

| | |
|---|---|
| DDDLTDSEMDVVRFD | SEQ ID NO: 37 |
| DDDLTDSEMDVVRYD | SEQ ID NO: 38 |
| DDDLTDSEMDVVRWD | SEQ ID NO: 39 |
| CDDDLTDSEMDVVRFDC | SEQ ID NO: 40 |
| AAALTDSEMDVVRFA | SEQ ID NO: 41 |

The invention also relates to any pharmaceutical composition characterized in that it comprises decoys as defined above, in combination with pharmaceutically acceptable vehicles.

Advantageously, the pharmaceutical compositions of the invention are presented in forms capable of being administered by parenteral route or by oral route.

Preferably the dose of said pharmaceutical compositions is such that it is comprised between approximately 1 and approximately 5 mg/kg/day of compounds of formula (I) or (II) defined above.

The invention also relates to the peptide sequences of formula (I) as defined.

A subject of the invention is also the peptide sequences of formula (II) as defined above.

The invention also relates to the products comprising:
at least one peptide sequence of formula (I) as defined above, and/or at least one peptide sequence of formula (II) as defined above,
and at least one compound chosen from the extracted, or recombinant factor VIII, or other derived products of human or animal origin,
as combination products to be used simultaneously, separately or spread over time, in factor VIII substitution therapy, within the framework of the treatment or prophylaxia of hemorragic accidents in patients suffering from hemophilia A.

A subject of the invention is also the pseudopeptides derived from the peptide sequences of formula (I) and (II) defined above, in particular the pseudopeptides obtained by conversion of one or more, or even all of the peptides of said peptide sequences to a D amino acid, which leads to a pseudopeptide considerably more resistant to proteolysis than the initial peptide [Kramer et al., 1998, Protein Eng 11, 941-8].

As regards the synthesis of the abovementioned compounds of formula (I) or (II), the latter is advantageously carried out in the following manner.

In the procedure for solid phase synthesis of a polypeptide, the desired polypeptide is synthesized starting with an insoluble support such as a benzhydryl-amine or chloromethylated resin (derived from a cross-linked polystyrene, and available from suppliers of chemical products).

The amino acid at the C-terminal of the polypeptide to be synthesized, the a nitrogen of which as well as the reactive sites are protected by protective groups, is bound to the resin using commonly-used strong coupling techniques. The protective group of the amine function is deprotected (leaving the other protective groups, if they exist, intact) in such a fashion that the following amino acid in the sequence (itself also having appropriate protective groups) is bound and so on. When the polypeptide is entirely synthesized, it is separated from its resin support, and all the protective groups are eliminated, then the polypeptide is recovered. Examples of appropriate protective groups: fluorenyl methyloxy carbonyl for the alpha amino, beta or gamma groups, tert-butyl ester for the aspartic and glutamic acids, tert-butyl oxy carbonyl for the lysine and tryptophan, trityl for the cysteine, asparagine, glutamine and histidine, tert-butyl for the serine and threonine, 2,2,4,6,7-pentadihydrobenzo furan for the arginine.

The invention is further illustrated using the detailed description which follows of the production of abovementioned compounds of formula (I) and (II), and of the demonstration of their ability to inhibit the anti-factor VIII antibodies.

I) Material and Methods

1) Techniques for Epitope-Variant-Type Peptide Decoys

Principle of the Spot Technique:

This parallel synthesis of peptides on Spot membrane (Frank, R. (1992) Spot Synthesis: an easy technique for the positionally addressable, parallel chemical synthesis on a membrane support, tetrahedron. 48, 9217-9232) makes it possible to rapidly obtain a large number of different peptides brought together simultaneously on a plane cellulose support. The peptides are prepared on a scale of the order of 50 nmol per spot, in immobilized form. On a sheet of cellulose (12-8 cm) chemically reactive circular sites (spots) are created, approximately 5 mm in diameter, which will serve as an anchorage point for binding the C-terminal amino acid of the peptide. The elongation of the peptide chain is carried out by successive additions of the amino acids of the C-terminal towards the N-terminal by esterification reaction. The aminated functions of the residues used are temporarily protected during coupling by a labile group (a 9-fluorenylmethyloxycarbonyl or Fmoc group) which is eliminated in basic medium. The reactive side chains are blocked by a stable group during the synthesis phase, and deprotected at the end of assembly. A synthesis cycle takes place in 4 stages: firstly formation of a peptide bond between the $NH_2$ of an amino acid already deposited and the COOH of the following amino acid, which is activated beforehand by N-hydroxybenzotriazole and N,N diisopropylcarbodiirnide. Secondly, the free $NH_2$ functions not having reacted are acetylated in order to avoid the formation of truncated peptides. Thirdly, the Fmoc protective group of the new amino acid is eliminated in basic medium by the piperidine. Fourthly, the aminated functions thus obtained are located with bromophenol blue. This cycle is repeated as many times as necessary. At the end of the synthesis, after having proceeded to the deprotection of the side chains of the amino acids, the peptides which remain bound in covalent manner to the membrane are analyzed by an indirect calorimetric immunoassay.

a) Preparation of the Membranes

The complete sequence of FVIII, with the exception of domain B, was synthesized on cellulose membrane in the form of overlapping pentadecapeptides frameshifted by 2 residues according to the Spot method. The general protocol has been described previously by Molina et al. (Molina, F., Laune, D., Gougat, C., Pau, B. & Granier, C. (1996) Improved performances of spot multiple peptide synthesis, *Pept Res.* 9, 151-5). The membranes are marketed by Abimed (Lagenfeld, Germany). The Fmoc amino acids and the N-hydroxybenzotriazole were ordered from Novabiochem. The robot which carries out the different coupling stages is an ASP222 robot (Abimed). All the peptides are acetylated on their N-terminal. Once the peptides are assembled, the protective groups of the side chains are deprotected by a treatment with trifluororacetic acid.

b) Indirect Calorimetric Immunological Test After saturation of the membrane in a blocking solution, the reactivity of the peptides is evaluated by immersion of the membrane in a solution of inhibitor antibodies to be tested, generally used at a concentration of 0.1-1 µg/ml. After washing, the peptide-antibodies interaction is developed by incubation of an anti-Fc antibody marked with alkaline phosphatase used at 1:1000 (Sigma), which in the presence of its substrate (BCIP-MTT-MgCl$_2$ Sigma) produces a blue precipitate at the level of the peptides having bound the antibody to be tested. The membranes are then regenerated in order to eliminate the blue precipitate and the bound antibody with a view to other tests.

c) Production of Analogue Epitopes

Once the epitope is identified, a series of analogue peptides is prepared in Spot synthesis by substituting each position of the reactive sequence by the 19 amino acids (with the exception of cysteine). The introduction of a constraint by the addition of a sulphur bridge also makes it possible to obtain analogue epitopes.

2) Technique for "Mimotope"-Type Peptide Decoys

Principle of the Phase Display Technique

Peptide ligands can be easily obtained thanks to their ability to bind to an antibody by using the phage-display technique (Smith, G. P. (1985) Filamentous fusion phage: novel expression vectors that display cloned antigens on the virion surface, *Science* 228, 1315-7), based on the presentation of random peptides at the surface of filamentous phages. These peptides can be exposed either at the surface of the pIII protein of the phages (maximum number 5 copies) or at the surface of the pVIII protein (maximum number 2700 copies). These peptides, varying widely in size (from 6AA up to 30AA) can be either linear or constrained by a sulphur bridge.

a) Different Peptide Phage Libraries Used

In order to carry out the screening of the random peptides, different libraries have been used:

4 peptide libraries, where the random peptide is expressed at the surface of the pVIII of the phage (a linear $15^{mer}$, a constrained $12^{mer}$, a semi-constrained $17^{mer}$ and a linear $30^{mer}$) The latter, described by L.L.C. Bonnycastle (University Burnaby, BC, Canada) (Bonnycastle, L. L., Mehroke, J. S., Rashed, M., Gong, X. & Scott, J. K. (1996) Probing the basis of antibody reactivity with a panel of constrained peptide libraries displayed by filamentous phage, *J Mol Biol*. 258, 747-62), are constituted approximately by $10^{13}$ TU/ml and constructed starting with the f88.4 vector, derived from the fd-tet phage.

2 peptide libraries, where the random peptide is expressed at the surface of the pIII of the phage (a linear $9^{mer}$ and a constrained $12^{mer}$). The latter are described by Dr Mazzucchelli L (Mazzucchelli, L., Burritt, J. B., Jesaitis, A. J., Nusrat, A., Liang, T. W., Gewirtz, A. T., Schnell, F. J. & Parkos, C. A. (1999) Cell-specific peptide binding by human neutrophils, *Blood* 93, 1738-48), and their diversity is of the order of $10^9$ TU/ml.

b) Screening of the Phage Library (Biopanning)

The biopanning technique is carried out following the abovementioned protocol described by Smith et al. Three rounds of selection and amplification are carried out, in parallel for the pIII and pVIII libraries. For each selection cycle, the different inhibitor antibodies, at a concentration of 1-5 µg/ml for the first 2 rounds, 0.1-0.5 µg/ml for the $3^{rd}$ round, in carbonate buffer (NaHCO$_3$, 100 mM, pH 8.6), are adsorbed on a 10×1.5 cm Petri dish (Falcon 1029) overnight at 4° C. under stirring. After five 2-minute washings with 0.05% TBS-T (Tris Buffered Saline: 1.37 M NaCl/26.8 mM KCl/0.5 M Tris base –0.05% Tween 20/pH 7) in order to eliminate the excess of antibodies, the non-specific sites are saturated for 2 hours at 37° C. with a solution of 0.1% TBS-T –3% BSA previously filtered. After elimination of this last solution by five 2-minute washings with 0.05% TBS-T, $2.10^{11}$ TU (transduction units) of each primary library, i.e. 100 times the diversity of each library, or eluate of phages originating from the preceding selection round are incubated overnight at 4° C. under stirring. The phages which are not retained are eliminated by ten 2-minute washings with 0.5% TBS-T followed by five 2-minute washings with 0.05% TBS-T. The phages retained are then eluted either by an acid elution (3 ml of HCl 0.1 M/glycine/BSA 1 mg/ml filtered previously/pH 2.2, incubation of 30 min at AT under stirring, then neutralization with 150 µl of 2 M Tris-HCl, pH 9) or by an elution by competition with FVIII (ON incubation at 4° C.). The different eluates are then used to infect *E. Coli* K91 cells for amplification. This amplification takes place in 2 stages: firstly 5 ml of a bacterial suspension in exponential growth phase (absorbance 1.8 to 550 nm) is added to each eluate. After incubation for 10 minutes at 37° C. without stirring, 93 ml of Luria-Bertani medium (LB) with 0.2 µg/ml of tetracycline (Tc) (pVIII libraries) or 0.75 µg/ml of kanamycin (Ka) (pIII libraries) are added and incubated for 30 minutes at 37° C. at 225 rpm. The concentration is then adjusted to 20 µg/ml for the Tc and 75 µg/ml for the Ka, then the suspension is incubated at 37° C. at 225 rpm overnight. These different bacterial suspensions are then centrifuged at 4° C. at 4000 rpm for 25 minutes, then at 8000 rpm for 12 minutes, in order to precipitate the bacteria. The supernatant containing the phages is taken up in poly (ethyleneglycol) 8000/2.5 M NaCl at a rate of 15 ml per 100 ml of supernatant; the precipitation is carried out overnight at 4° C. After centrifugation at 4° C. at 8000 rpm for 40 minutes, the pellet is taken up in 3 ml of 50 mM TBS/NaCl, and incubated at 37° C. for 30 minutes at 150 rpm. The content is transferred into 3 eppendorfs, centrifuged at 15000 rpm for 10 minutes at 4° C. in order to eliminate the cell debris, then transferred into sterile 1.5-ml vials and stored at –80° C.

At each selection stage, the quantity of amplified phages is evaluated by titration, whilst the enrichment with related phages is evaluated by ELISA. After 3 selection rounds, 3 cloning stages made it possible to obtain on solid medium (LB-agar-Tc medium at 20 µg/ml or Ka at 75 µg/ml) isolated bacterial colonies. The ability of the different clones to bind specifically to the inhibitor antibodies is then tested by ELISA.

c) Direct Elisa: Test of the Recognition of Inhibitor Antibodies by the Phages

The different inhibitor antibodies used for the screening of libraries are immobilized at 1 µg/ml in NaHCO$_3$ buffer on a microtitration plate (Nunc) overnight at 4° C. The wells are saturated with 0.1% PBS-T-2% milk for 1 hour 30 minutes at 37° C. The phages originating from the different pannings, diluted to 1/25 in 0.1% PBS-T-2% milk buffer are then incubated for 1 hour 30 minutes at 37° C. Between each of these incubations, 3 washings with 0.1% PBS-T are carried out except after saturation. The bound phages are detected using an anti-M13 antibody coupled to peroxidase (Amersham Boehringer) diluted to 1:3000, incubated for 1 hour at 37° C. After 5 washings, the peroxidase substrate (OPD) is added. The reaction takes place over 30 minutes in the dark then an absorbance measurement is carried out at 450 nm. After stopping the reaction by the addition of 4N H$_2$SO$_4$, a new measurement is carried out at 490 nm.

The specificity of the phages is demonstrated by the absence of reactivity with irrelevant antibodies.

d) Determination of the Oligonucleotide Sequence

The sequencing of the DNA originating from the phages is carried out on an automatic sequencer (EUROGENTEC). The primers used: 5' GTT TTG TCG TCT TTC CAG ACG 3' (SEQ ID NO: 42) for the pIII, and 5' TCG GCA AGC TCT TTT AGG 3' (SEQ ID NO: 43) for the pVIII, are localized downstream of the peptide insert.

3) Ability of the epitope or mimotope variant peptides in soluble form to inhibit their inhibitor antibodies in vitro and ex vivo a) Synthesis of Soluble Peptides The different epitopes identified in Spot or the mimotopes determined by the phage display technique are then synthesized in the form of soluble synthetic peptides using an Abimed AMS422 synthesizer based on Fmoc chemistry in soluble phase (Gausepohl, H., Boulin, C., Kraft, M. & Frank, R. W. (1992) Automated multiple peptide synthesis, *Pept Res.* 5, 315-20). The peptides are deprotected and cleaved from the resin by a treatment with trifluoroacetic acid in the presence of appropriate scavengers. The peptides are then lyophilized, and their purity is evaluated by HPLC. If necessary, the peptides are purified in order to obtain more than 90% homogeneity by HPLC.

b) Neutralizing Ability of the Decoys In Vitro

The FVIII is immobilized on the ON plate at 4° C. In parallel, the inhibitor antibody is preincubated with its epitope peptide(s) in the ON range at 4° C. in 0.1% PBS-T-2% milk. After saturation for 1 hour with 0.1% PBS-T-2% milk, the Ab-peptide mixtures are incubated with the immobilized FVIII for 2 hours at 37° C. Between each of these incubations, 3 washings with 0.1% PBS-T are carried out except after the saturation. Detection of the FVIII-Ab complex is achieved by a mouse or human anti-IgG coupled to peroxidase diluted to 1:3000 incubated for 1 hour at 37° C. After 5 washings with 0.1% PBS-T, the peroxidase substrate (OPD) is added. The reaction takes place for 30 minutes in the dark then measurement of the absorbance is carried out at 450 nm. After stopping the reaction by the addition of $H_2SO_4$ 4N, a new measurement is carried out at 490 nm.

c) Neutralizing Ability of the Decoys in a Functional Test (Bethesda Test)

This functional test (Kasper, C. K. & Pool, J. G. (1975) Letter: Measurement of mild factor VIII inhibitors in Bethesda units, *Thromb Diath Haemorrh.* 34, 875-6) consists of measuring the time necessary for a mixture composed of different coagulation factors (FIXa, FVIII, phospholipides, calcium etc.) in order to coagulate completely. The inhibiting effect of an antibody is characterized in such a test by an extension of the coagulation time, the inhibiting ability of the antibody becomes greater as the extension of the coagulation time increases. The inhibiting character of an antibody is expressed in Bethesda units, which corresponds to the reciprocal concentration of antibodies in order to neutralize 50% of the coagulant activity of the FVIII. In contrast, the neutralizing effect of the peptides is translated by a return to the initial coagulation time obtained in the absence of inhibitor.

The functional test followed is derived from the abovementioned test described by Kasper. The anti-FVIII monoclonal antibodies are diluted in an 0.05 M imidazole buffer, pH 7.3. An equal volume of this preparation (250 µl) with normal plasma buffered in imidazole (0.1 M, pH 7.4) are mixed and incubated for 2 hours at 37° C. Similarly, normal plasma buffered in imidazole is mixed with a non-specific antibody which constitutes the control. The inhibiting activity of an antibody is read from a semi-logarithmic graph representing the correlation between the residual activity of the FVIII and the inhibiting activity.

In order to demonstrate the ability of the peptides to neutralize the inhibitor antibodies, the inhibitor antibody used at a concentration so as to obtain 50% of residual FVIII, is preincubated ON at 4° C. in imidazole buffer with increasing peptide concentrations. This mixture is then treated as above.

II) DETAILED DESCRIPTION

1) Choice of Antibodies:

The following were used:

a mouse monoclonal antibody, hereafter called ESH8, which has a very considerable neutralization activity of the procoagulant activity df the FVIII (6300 Besthesda Units/mg [Scandella et al., 1995, Blood 86, 1811-9]). This antibody is a good representative of the human antibodies binding to the C2 domain of factor VIII, a 2C11 human monoclonal antibody (Jacquemin et al., 1998, abovementioned), several mouse monoclonal antibodies, hereafter called F7B4, F29F11, F14A12, F18B1, F19C2 and F21 C1 which represent a model of the human antibodies binding to the $a_1$ acid region of factor VIII for the first 3, and the $a_3$ acid region for the latter.

2) Processes for Obtaining Decoys:

"Epitope variant"-type peptide decoys were obtained, by using the Spot technique in order to introduce variations of the epitope's amino acids sequence. The epitope variant peptides retain the reactivity with the antibody or can show a stronger reactivity than the epitope. For example, such an approach concerning the $D^{356}VVRF^{360}$ epitope (SEQ ID NO: 46) of the anti-FVIII F7B4 antibody has shown that the $F^{360}$ could be substituted without loss of reactivity by the 2 other aromatic amino acids W and Y. In another example, the presentation of the epitope in cyclic form was evaluated with the CDDDLTDSEMDVVRFDC peptide (SEQ ID NO: 40) and the importance of the negative charges was studied with the AAALTDSEMDVVRFA peptide (SEQ ID NO: 41). All these "epitope variant"-type decoys were obtained by standard peptide synthesis and their binding activity to the anti-factor viii antibody measured.

"Mimotope"-type peptide decoys were obtained by the recombinant phage library technique. The approach of selection of peptides from random libraries of sequences has been described [Smith et al., 1993, Methods Enzymol. 217, 228-257]. Peptides carried by the filamentous phages at the surface of their envelope protein (pVIII or pIII) can be used: for example, a library coding for peptides with 15 amino acids, and another coding for peptides with 12 amino acids, structurally constrained by the constant presence of two cysteine residues. The conditions for selection of the phages used are those described (in particular by [Ferrières et al., 2000, Eur. J. Biochem. 267, 1819-1829]). The elution of the phages specifically captured by the antibody is carried either by acid treatment or by displacement with an excess of antigen. The amino acid sequence of each peptide selected can be determined as described in particular by Ferrières et al. For example, mimotope peptides with the ESH8 antibody, as well as with the 2C11 human antibody could be obtained. Depending on the elution condition used, the consensus motifs obtained vary. By acid elution, two groups of sequences, all originating from the constrained library of 12 amino acids, are obtained: the first, of mimotope type, comprises a single sequence YCNPSIGDKNCR (SEQ ID NO: 2), a sequence represented by 3 clones, the second group of epitope type is distinguished by a consensus motif: X-C-X- hydrophobic-aromatic (Y/F)-G-K-T-X-L-C-X (where x represents any amino acid) (SEQ ID NO: 47), which has a homology of sequence with the C2 domain of factor VIII. This consensus motif is found again in 6 different sequences: ECIVYGK-TALCT (SEQ ID NO: 3) (represented once), QCQTFGKT-MLCT (SEQ ID NO: 44) (4 times), SCRLFGKTYLCH (SEQ ID NO: 5) (once), SCTVYGKTPLCG (SEQ ID NO: 6) (11 times), RCKTFGKTTLCS (SEQ ID NO: 7) (once) and RCTVYGKTVLCL (SEQ ID NO: 8) (once). Whereas with elution with the antigen, a single sequence is obtained and it originates from the linear library of 15 amino acids KPGEV-PRHRVTDFDR (SEQ ID NO: 45), represented 4 times.

In order to verify that these sequences taken outside the context of the phage are still reactive with the ESH8 antibody, these have been synthesized on membrane by the Spot technique. It transpires that all have retained their reactivity. Then, in order to determiner the key residues of the ESH8/peptide bond, each amino acid of the peptide was substituted by the other 19 amino acids (with the exception of cysteine) in order to determine 1) which were the residues critical to the ESH8/peptide bond, 2) any tolerable substitutions which make it possible to release a common characteristic (for example hydrophobic or aromatic character, presence of a long side chain). The residues such as glycine (G), lysine (K), threonine (T) and leucine (L) do not tolerate any substitution, in contrast, with respect to the hydrophobic residue, the more reactive elements are valine (V), isoleucine (I) and leucine (L), but completely accept residues such as threonine (T), methionine (M), phenylalanine (F), tryptophan (W), and tyrosine (Y). With respect to the aromatic residue, this position mainly tolerates phenylalanine (F), and tyrosine (Y) with a slight acceptance of tryptophan (W).

Once these sequences are identified, a decoy is obtained by standard peptide synthesis.

3) Processes for Determining the Blocking Activity of the Decoys:

The blocking activity of the decoys can be verified in vitro in an ELISA test. The format used makes it possible to demonstrate the inhibition of the binding of the inhibitor antibody to factor VIII by the decoy introduced in an increasing concentration. The neutralizing ability of the decoy can be confirmed in a functional test such as the Bethesda Test (method of Kasper, [Kasper et al., 1975, Thromb. Diath. Haemorrh. 34, 875-6]).

The 7 soluble mimotope peptides more particularly studied are the following:

| 103 | KCGRWSNRSSCT | SEQ ID NO: 17 |
| 104 | ECGSHAWGRRCK | SEQ ID NO: 33 |
| 105 | CSKWHNRSKRHC | SEQ ID NO: 13 |
| 106 | CMKWSNRSSRWC | SEQ ID NO: 16 |
| 107 | SCHAWSNRRTCR | SEQ ID NO: 10 |
| 108 | QCHTWSNRRSCL | SEQ ID NO: 9 |
| 109 | RCHAWSNRKSCV | SEQ ID NO: 11 |

The Inventors studied the ability of these soluble peptides to inhibit the binding of the 2C11 antibody to factor VIII in an ELISA test in vitro in the following manner: immobilization of FVIII, pre-incubation of 2C11 with the soluble peptides in the range (200 µM, 20 µM, 2 µM, 200 nM, 20 nM, 2 nM) overnight at 4° C., then incubation of this premixture on the FVIII, then development of the 2C11 antibody. The results obtained are indicated hereafter.

| % inhibition | 103 | 104 | 105 | 106 | 107 | 108 | 109 |
|---|---|---|---|---|---|---|---|
| 200 | 62.73 | 63.71 | 75.58 | 36.56 | 90.48 | 60.69 | 75.05 |
| 20 | 28.26 | 30.68 | 45.04 | 21.99 | 80.04 | 25.99 | 37.48 |
| 2 | 3.47 | 13.44 | 10.27 | 0.00 | 37.33 | 15.79 | 12.46 |
| 0.02 | 0 | 0 | 0 | 0 | 0 | 0 | 0 |
| 0.002 | 0 | 0 | 0 | 0 | 0 | 0 | 0 |

All the peptides tested inhibit the 2C11 Ab/FVIII bond, peptide 107 proving to be the most effective.

4) Ability of peptide 107 (SCHAWSNRRTCR) (SEQ ID NO: 10) to neutralize the 2C11 antibody in functional and in vivo analyses.

As peptide 107 has proved to be a peptide which is relatively effective at inhibiting the FVIII-2C11 antibody bond, the Inventors have taken a more detailed interest in its ability to neutralize the inhibiting activity of 2C11.

Firstly, the Inventors evaluated in a functional coagulation test (Bethesda test) the ability of peptide 107 to restore the procoagulant activity of FVIII in the presence of 2C11. FIG. 2 depicts the dose-dependent neutralization of the inhibiting activity of 2C11 by peptide 107. At a 2C11 concentration of 3.5 nM, a concentration at which 98% of the activity of the FVIII is inhibited (FIG. 1), the total neutralization of its inhibiting effect is. achieved with a peptide 107 concentration of the order of 100 µM, the $IC_{50}$ being equal to 19 µM. A control peptide used in an identical concentration range has no neutralizing effect (FIG. 2). Peptide 107 incubated with FVIII alone does not at all modify the procoagulant activity of the FVIII (FIG. 2). The peptides (103, 104, 105, 106, 108, and 109) can also effectively neutralize the inhibiting activity of 2C11. However, higher peptide concentrations are necessary in order to achieve an effectiveness similar to that of peptide 107 (data not shown).

Figure 3:
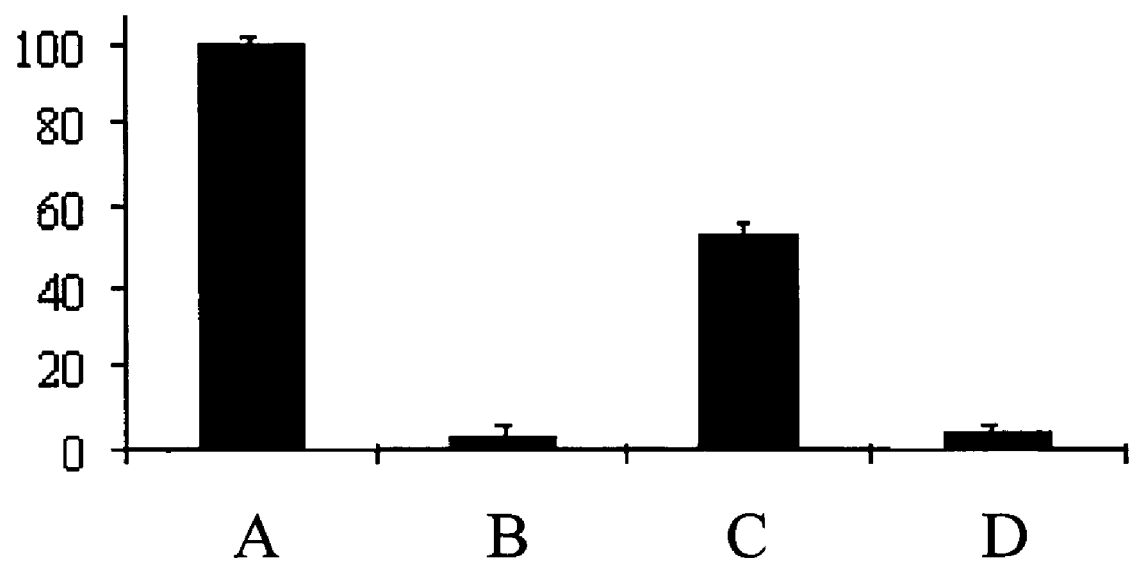

Secondly, the neutralization properties of peptide 107 were studied in vivo, using a mouse model deficient in FVIII. A preliminary study made it possible to specify that an intravenous administration of 0.5 UI of human recombinant FVIII to such mice made it possible to obtain an FVIII plasma count of the order of 0.3 IU/ml FVIII, a count which is stable for at least one hour. Having determined this, 2C11 antibody (16.7 nM) incubated alone, in the presence of peptide 107, or a control peptide (650 µM and 700 µM, respectively) was injected into the tail vein of three groups of mice respectively. Thirty minutes later, the FVIII plasma count of these mice was reconstituted by the injection of 0.5 UI of human FVIII and after fifteen minutes the plasma procoagulant activity was measured. FIG. 3 proves that the administration of 2C11 alone completely inhibits the procoagulant activity of the FVIII injected, whereas the mice which have received the 2C11 antibody in the presence of peptide 107 maintain 52% of the procoagulant activity of the FVIII. The neutralizing activity of peptide 107 is very specific, since a control peptide has no neutralizing effect.

Therefore, these data indicate that the ability of peptide 107 to neutralize the inhibition of the 2C11 antibody vis-à-vis FVIII, suggested by in vitro experiments, is also verified under in vivo conditions, which resemble hemophilia A.

Thirdly, the Inventors looked at whether the neutralizing properties of peptide 107 vis-à-vis 2C11 could also be applied to other serums of hemophilia patients with inhibitors. A preliminary study reveals that out of 12 serums of hemophilia patients with inhibitors, 2 of them react with peptide 107 thus indicating that FVIII inhibitors similar to 2C11 are produced by other patients with hemophilia A.

FIG. 1

Figure 2:
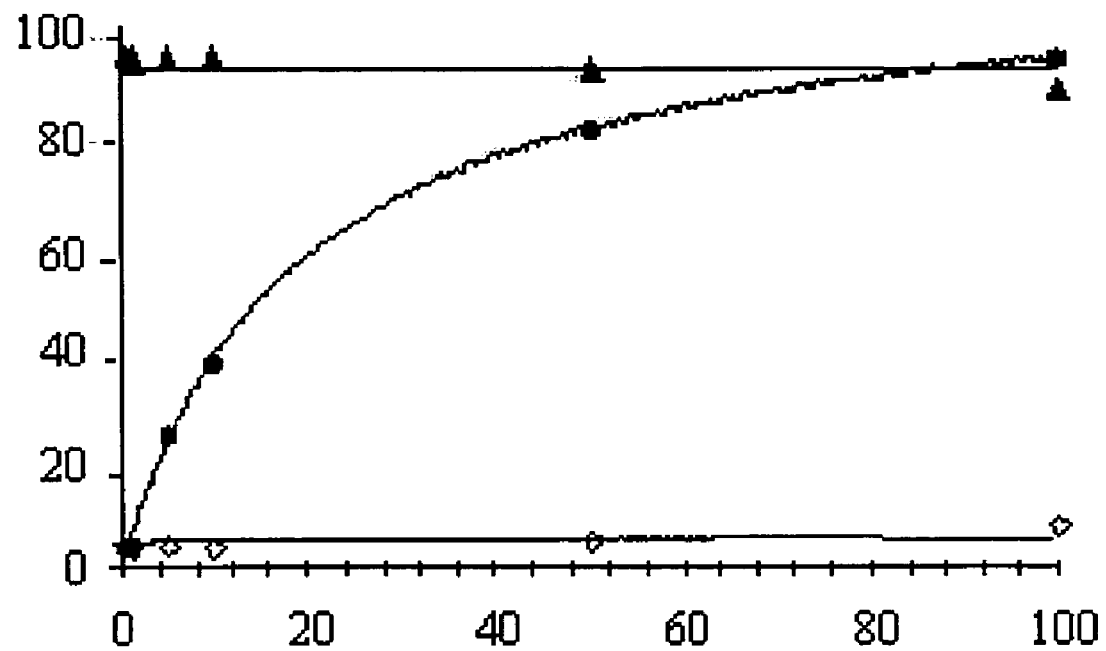

FIG. 1 represents the effect of the 2C11 antibody on the activity of factor VIII evaluated by the Bethesda test. Factor VIII was incubated in the presence of 3.5 nM of 2C11 antibody for 2 hours at 37° C., the residual activity of factor VIII was then measured with a coagulometer, in one stage.

The percentage of residual activity of factor VIII is represented on the Y-axis. Bar A represents the activity of the factor VIII alone (100%), Bar B represents the factor VIII activity in the presence of the 2C11 antibody at a concentration of 3.5 nM.

In the presence of 3.5 nM of 2C11 factor VIII activity is inhibited almost completely.

FIG. 2

FIG. 2 represents the evolution of the activity of factor VIII, evaluated by the Bethesda test, in the presence of 3.5 nM of 2C11 antibody as a function of peptide concentration. The 2C11 antibody was incubated overnight at 4° C. in the presence of a control peptide or peptide 107 (SCHAWSNR-RTCR) (SEQ ID NO: 10) in variable concentration. The factor VIII was then incubated for 2 hours at 37° C. with these peptide-antibody mixtures or with peptide 107 alone, then its residual activity was measured with a coagulometer, in one stage.

The percentage of residual activity of factor VIII is represented on the Y-axis, the peptide concentration is represented on the X-axis (µM). The black triangles represent the evolution of the residual activity of factor VIII in the presence of increasing concentrations of peptide 107 alone, the black dots represent the evolution of the residual activity of factor VIII in the presence of the mixture of increasing concentrations of peptide 107 and the 2C11 antibody, the white diamonds represent the evolution of the residual activity of factor VIII in the presence of the mixture of increasing concentrations of the control peptide and the 2C11 antibody.

Peptide 107 makes it possible to neutralize the effect of the 2C11 antibody.

FIG. 3

FIG. 3 represents the effect of the injection of the 2C11 antibody in the absence or in the presence of peptide 107 or of a control peptide on the blood coagulation of mice deficient in factor VIII and to which human factor VIII is administered.

The 2C11 antibody (16.5 nM) or a mixture containing the 2C11 antibody (16.5 nM) and peptide 107 (650 µM) or a control peptide (700 µM) was injected into the tail vein of a "knock out" mouse, deficient in factor VIII, at a rate of 2.5 µg of 2C11 antibody, 1 mg of peptide 107 and 1 mg of control peptide. After 30 minutes, 0.5 UI of human factor VIII was injected and the plasma procoagulant activity was then measured by a chromogenic test 15 minutes later.

The percentage of residual activity of factor VIII is represented on the Y-axis. Bar A represents the effect of the injection of factor VIII without prior injection of antibodies (100% of residual activity). Bar B represents the effect of the injection of the 2C11 antibody alone prior to the injection of factor VIII. Bar C represents the effect of the injection of a mixture of 2C11 antibody and peptide 107 prior to the injection of factor VIII. Bar D represents the effect of the injection of a mixture of the 2C11 antibody and a control peptide prior to the injection of factor VIII.

Peptide 107 specifically neutralizes the effect of the 2C11 antibody in vivo.

The invention claimed is:

1. A method for the treatment of a disorder linked to the appearance of antibodies against endogenous factor VIII, exogenous factor VIII, derivatives thereof, recombinant or non-recombinant versions thereof, or in subjects suffering from hemophilia A, said method comprising administering mimotope decoys of factor VIII to said subjects, wherein said mimotope decoys of factor VIII are of the formula:

$$(X_1)_{n1}\text{-C-}X_7\text{-}X_8\text{-W-}X_9\text{-N-R-}X_{10}\text{-}X_{11}\text{-}(X_{12})n_{13}\text{-C-}(X_2)_{n2},$$

in which:

$n_1$, $n_2$, $n_{12}$ and $n_{13}$ each independently represent 0 or 1;
$X_1$ is Y,E,Q,S,R,A,K,N, or T;
$X_2$ is R,T,H,G,S,L,V,P,F,D,K,A,Q or I;
$X_7$ is H, S, T, M, Q, or G;
$X_8$ is T, A, K, R, Q, or E;
$X_9$ is S, A, H, F, V, G, or T;
$X_{10}$ is R, K, L, S, H, T, I, or A;
$X_{11}$ is S, T, V, K, R, Y, M, or D;
$X_{12}$ is S, R, or L; and
$X_{11}$ is I, H, or W.

2. The method of claim 1, wherein said mimotope decoys are selected from the group consisting of:

QCHTWSNRRSCL; (SEQ ID NO: 9)
SCHAWSNRRTCR; (SEQ ID NO: 10)
RCHAWSNRKSCV; (SEQ ID NO: 11)
CSKWANRLVSIC; (SEQ ID NO: 12)
CSKWHNRSKRHC; (SEQ ID NO: 13)

-continued

ACTTWSNRSKCP; (SEQ ID NO: 14)
ECTRWSNRSRCF; (SEQ ID NO: 15)
CMKWSNRSSRWC; (SEQ ID NO: 16)
KCGRWSNRSSCT; (SEQ ID NO: 17)
CGRWFNRSDLHC; (SEQ ID NO: 18)
ACHEWSNRSTCT; (SEQ ID NO: 19)
KCSRWTNRHLCD; (SEQ ID NO: 20)
KCTRWTNRHLCS; (SEQ ID NO: 21)
KCTRWTNRAHCP; (SEQ ID NO: 22)
QCSKWVNRSRCA; (SEQ ID NO: 23)
NCQKWTNRRTCL; (SEQ ID NO: 24)
QCGRWSNRSYCS; (SEQ ID NO: 25)
TCHRWGNRTSCQ; (SEQ ID NO: 26)
QCHRWANRISCS; (SEQ ID NO: 27)
RCTQWTNRAYCP; (SEQ ID NO: 28)
ACTQWSNRHMCG; (SEQ ID NO: 29)
and
TCHPFSNRSTCT; (SEQ ID NO: 30).

3. The method of claim 2, wherein the mimotope decoy is SCHAWSNRRTCR (SEQ ID NO: 10).

* * * * *

```
                       SEQUENCE LISTING

<160> NUMBER OF SEQ ID NOS: 49

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Pro Ser Ile Gly Asp Lys Asn
 1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Tyr Cys Asn Pro Ser Ile Gly Asp Lys Asn Cys Arg
 1               5                  10

<210> SEQ ID NO 3
<211> LENGTH: 12
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 3

Glu Cys Ile Val Tyr Gly Lys Thr Ala Leu Cys Thr
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln Cys Pro Thr Phe Gly Lys Thr Met Leu Cys Thr
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Cys Arg Leu Phe Gly Lys Thr Tyr Leu Cys His
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Cys Thr Val Tyr Gly Lys Thr Pro Leu Cys Gly
 1               5                  10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Cys Lys Thr Phe Gly Lys Thr Thr Leu Cys Ser
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Cys Thr Val Tyr Gly Lys Thr Val Leu Cys Leu
 1               5                  10
```

```
<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gln Cys His Thr Trp Ser Asn Arg Arg Ser Cys Leu
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Cys His Ala Trp Ser Asn Arg Arg Thr Cys Arg
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Cys His Ala Trp Ser Asn Arg Lys Ser Cys Val
 1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Cys Ser Lys Trp Ala Asn Arg Leu Val Ser Ile Cys
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Ser Lys Trp His Asn Arg Ser Lys Arg His Cys
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

```
Ala Cys Thr Thr Trp Ser Asn Arg Ser Lys Cys Pro
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Cys Thr Arg Trp Ser Asn Arg Ser Arg Cys Phe
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Met Lys Trp Ser Asn Arg Ser Ser Arg Trp Cys
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Lys Cys Gly Arg Trp Ser Asn Arg Ser Ser Cys Thr
 1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Cys Gly Arg Trp Phe Asn Arg Ser Asp Leu His Cys
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Cys His Glu Trp Ser Asn Arg Ser Thr Cys Thr
 1               5                  10

<210> SEQ ID NO 20
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 20

Lys Cys Ser Arg Trp Thr Asn Arg His Leu Cys Asp
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Cys Thr Arg Trp Thr Asn Arg His Leu Cys Ser
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Lys Cys Thr Arg Trp Thr Asn Arg Ala His Cys Pro
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Cys Ser Lys Trp Val Asn Arg Ser Arg Cys Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Cys Gln Lys Trp Thr Asn Arg Arg Thr Cys Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Cys Gly Arg Trp Ser Asn Arg Ser Tyr Cys Ser
1               5                   10
```

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Cys His Arg Trp Gly Asn Arg Thr Ser Cys Gln
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Cys His Arg Trp Ala Asn Arg Ile Ser Cys Ser
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Cys Thr Gln Trp Thr Asn Arg Ala Tyr Cys Pro
 1               5                  10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Cys Thr Gln Trp Ser Asn Arg His Met Cys Gly
 1               5                  10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Cys His Pro Phe Ser Asn Arg Ser Thr Cys Thr
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 31

Lys Cys Glu Pro Asp Asp Pro Trp Pro Gln Cys Ile
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Cys Lys Arg Asn His Arg Trp Gly Ala Cys Val
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Glu Cys Gly Ser His Ala Trp Gly Arg Arg Cys Lys
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ala Cys Lys Arg Asn His Arg Trp Gly Ala Cys Val
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Cys Gly Ser His Ala Trp Gly Arg Arg Cys Lys
 1               5                  10

<210> SEQ ID NO 36
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Asp Asp Leu Thr Asp Ser Glu Met Asp Val Val Arg Phe Asp
 1               5                  10                  15

<210> SEQ ID NO 37
<211> LENGTH: 15
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 37

Asp Asp Asp Leu Thr Asp Ser Glu Met Asp Val Val Arg Phe Asp
 1               5                  10                  15

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Asp Asp Asp Leu Thr Asp Ser Glu Met Asp Val Val Arg Tyr Asp
 1               5                  10                  15

<210> SEQ ID NO 39
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Asp Asp Asp Leu Thr Asp Ser Glu Met Asp Val Val Arg Trp Asp
 1               5                  10                  15

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Asp Asp Asp Leu Thr Asp Ser Glu Met Asp Val Val Arg Phe Asp
 1               5                  10                  15

Cys

<210> SEQ ID NO 41
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Ala Ala Leu Thr Asp Ser Glu Met Asp Val Val Arg Phe Ala
 1               5                  10                  15

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
```

```
gttttgtcgt ctttccagac g                                          21
```

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
tcggcaagct cttttagg                                              18
```

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Cys Gln Thr Phe Gly Lys Thr Met Leu Cys Thr
 1               5                  10

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Lys Pro Gly Glu Val Pro Arg His Arg Val Thr Asp Phe Asp Arg
 1               5                  10                  15

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Val Val Arg Phe
 1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      consensus motif
<220> FEATURE:
<221> NAME/KEY: MOD_RES
<222> LOCATION: (1)
<223> OTHER INFORMATION: Tyr or Phe
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (8)
<223> OTHER INFORMATION: Variable amino acid

<400> SEQUENCE: 47

```
Xaa Gly Lys Thr Xaa Leu Cys Xaa
 1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: Synthetic
      formula sequence
<220> FEATURE:
<221> NAME/KEY: MOD_RES
<222> LOCATION: (1)
<223> OTHER INFORMATION: Variable amino acid or not present
<220> FEATURE:
<221> NAME/KEY: MOD_RES
<222> LOCATION: (2)
<223> OTHER INFORMATION: Any hydrophobic amino acid
<220> FEATURE:
<221> NAME/KEY: MOD_RES
<222> LOCATION: (3)
<223> OTHER INFORMATION: Any aromatic amino acid
<220> FEATURE:
<221> NAME/KEY: METAL
<222> LOCATION: (7)
<223> OTHER INFORMATION: Any hydrophobic amino acid

<400> SEQUENCE: 48

Xaa Xaa Xaa Gly Lys Thr Xaa Leu
 1               5

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      formula sequence
<220> FEATURE:
<221> NAME/KEY: MOD_RES
<222> LOCATION: (1)
<223> OTHER INFORMATION: Cys or not present
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (15)..(16)
<223> OTHER INFORMATION: Variable amino acid
<220> FEATURE:
<221> NAME/KEY: MOD_RES
<222> LOCATION: (17)
<223> OTHER INFORMATION: Cys or not present

<400> SEQUENCE: 49

Cys Xaa Xaa Xaa Leu Thr Asp Ser Glu Met Asp Val Val Arg Xaa Xaa
 1               5                  10                  15
Cys
```